US006715491B2

(12) United States Patent
Cooper et al.

(10) Patent No.: US 6,715,491 B2
(45) Date of Patent: *Apr. 6, 2004

(54) MAGNETICALLY ORIENTING LARYNGEAL ELEVATOR BLADE

(75) Inventors: Ivan N. Cooper, Knoxville, TN (US); Matthew Sellers, Knoxville, TN (US); Bruce L. Fariss, Knoxville, TN (US)

(73) Assignee: Ibionics Corporation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/207,602

(22) Filed: Jul. 29, 2002

(65) Prior Publication Data

US 2003/0154985 A1 Aug. 21, 2003

Related U.S. Application Data

(63) Continuation-in-part of application No. 10/078,133, filed on Feb. 19, 2002.

(51) Int. Cl.[7] .............................................. A61M 25/00
(52) U.S. Cl. ............................. 128/207.14; 128/200.26
(58) Field of Search ..................... 128/200.26, 207.14, 128/207.15, 207.29

(56) References Cited

U.S. PATENT DOCUMENTS

| | | | | | |
|---|---|---|---|---|---|
| 2,463,149 A | * | 3/1949 | Caine | .................... | 128/200.26 |
| 2,541,402 A | * | 2/1951 | Caine | .................... | 128/200.26 |
| 2,862,498 A | * | 12/1958 | Weekes | .................. | 128/207.14 |
| 3,314,431 A | * | 4/1967 | Smith, Jr. | .............. | 128/200.26 |
| 3,674,014 A | | 7/1972 | Tillander | | |
| 3,996,939 A | * | 12/1976 | Sheridan et al. | ........ | 128/207.14 |
| 4,063,561 A | * | 12/1977 | McKenna | ............. | 128/207.15 |
| 4,244,362 A | | 1/1981 | Anderson | ............. | 128/200.26 |
| 4,431,005 A | * | 2/1984 | McCormick | ................ | 600/433 |
| 4,444,185 A | * | 4/1984 | Shugar | ................... | 128/207.29 |
| 4,445,501 A | * | 5/1984 | Bresler | ......................... | 600/12 |
| 4,567,882 A | * | 2/1986 | Heller | ......................... | 600/249 |
| 4,593,687 A | * | 6/1986 | Gray | .................... | 128/200.26 |
| 4,865,586 A | * | 9/1989 | Hedberg | .................. | 604/93.01 |
| 4,913,139 A | | 4/1990 | Ballew | | |
| 4,943,770 A | * | 7/1990 | Ashley-Rollman et al. | ...... | 324/207.17 |
| 5,235,970 A | * | 8/1993 | Augustine | .............. | 128/200.26 |
| 5,257,636 A | * | 11/1993 | White | ........................ | 128/897 |
| 5,390,661 A | | 2/1995 | Griffith et al. | | |
| 5,429,131 A | | 7/1995 | Scheinman et al. | | |
| 5,560,351 A | * | 10/1996 | Gravenstein et al. | .. | 128/200.26 |
| 5,775,322 A | | 7/1998 | Silverstein et al. | | |
| 5,785,051 A | * | 7/1998 | Lipscher et al. | ....... | 128/207.15 |
| 5,996,582 A | * | 12/1999 | Turnbull | ................ | 128/207.29 |
| 6,013,038 A | | 1/2000 | Pflueger | | |
| 6,157,853 A | | 12/2000 | Blume et al. | | |
| 6,161,537 A | * | 12/2000 | Gravenstein et al. | .. | 128/200.26 |
| 6,173,199 B1 | | 1/2001 | Gabriel | | |
| 6,349,720 B1 | * | 2/2002 | Clark | .................... | 128/200.26 |
| 6,553,993 B2 | * | 4/2003 | Toti et al. | .............. | 128/207.14 |

\* cited by examiner

Primary Examiner—Aaron J. Lewis
(74) Attorney, Agent, or Firm—Pitts & Brittian, P.C.

(57) ABSTRACT

A magnetic intubation apparatus insertable into an opening in a patient for guiding a tube into a preferred passageway within the patient. The magnetic intubation apparatus includes a flexible elongated body having an insertion end sized to be inserted through the patient's internal passageways. A magnetic member is coupled to the insertion end in a pivotable relationship. During insertion into the patient, the insertion end having the magnetic member thereon is guided into a preferred passageway such as the trachea or the esophagus by manipulating an external magnetic field disposed proximal to the patient. A method for insertion is also disclosed, providing for positioning within a patient of an elongated body having a magnetic member coupled to an insertion end that is guided by an external magnetic field into the preferred passageway within the patient for intubation of a tube into the preferred passageway.

22 Claims, 6 Drawing Sheets

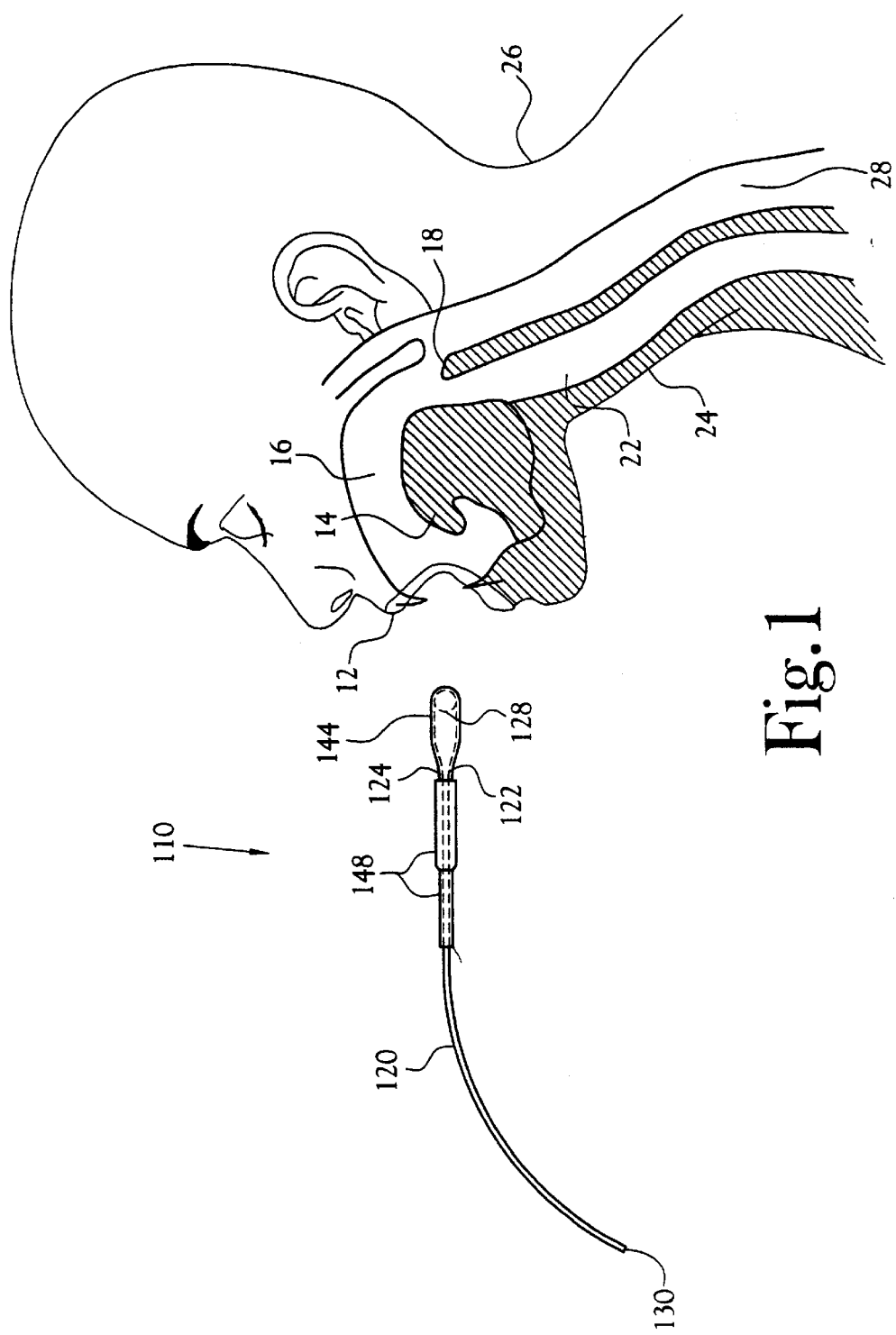

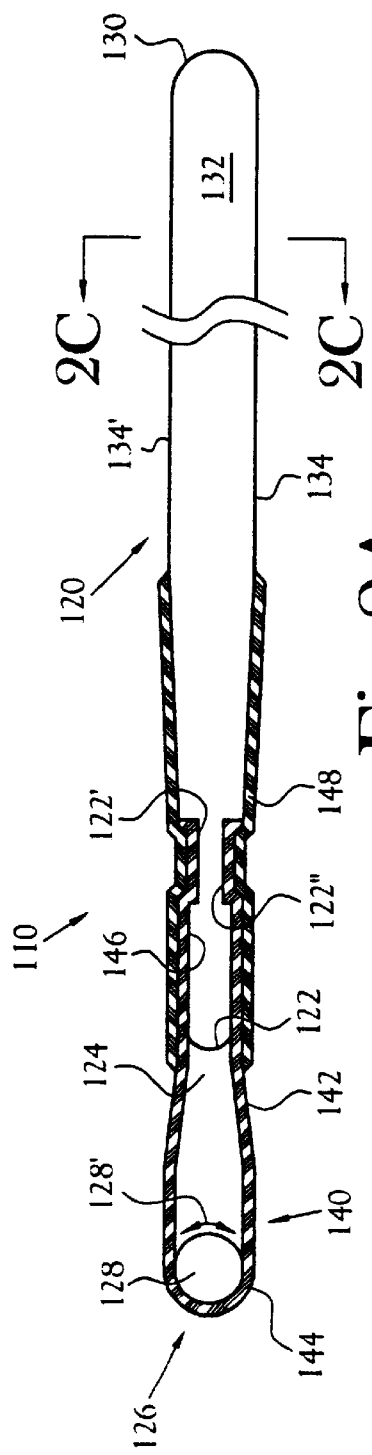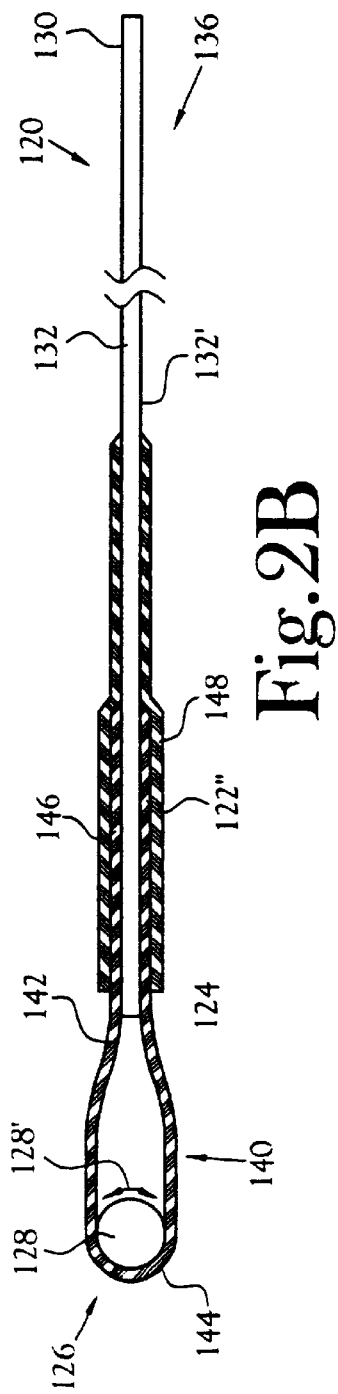

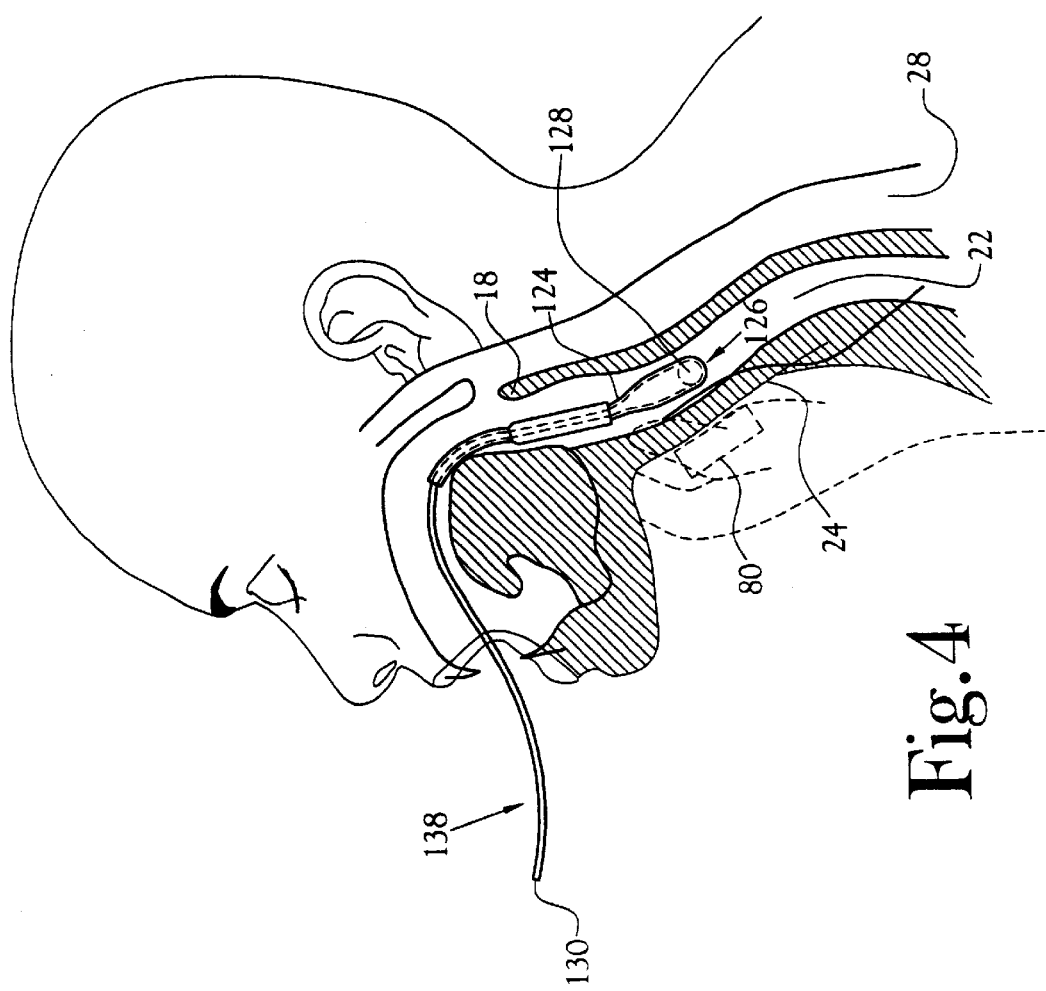

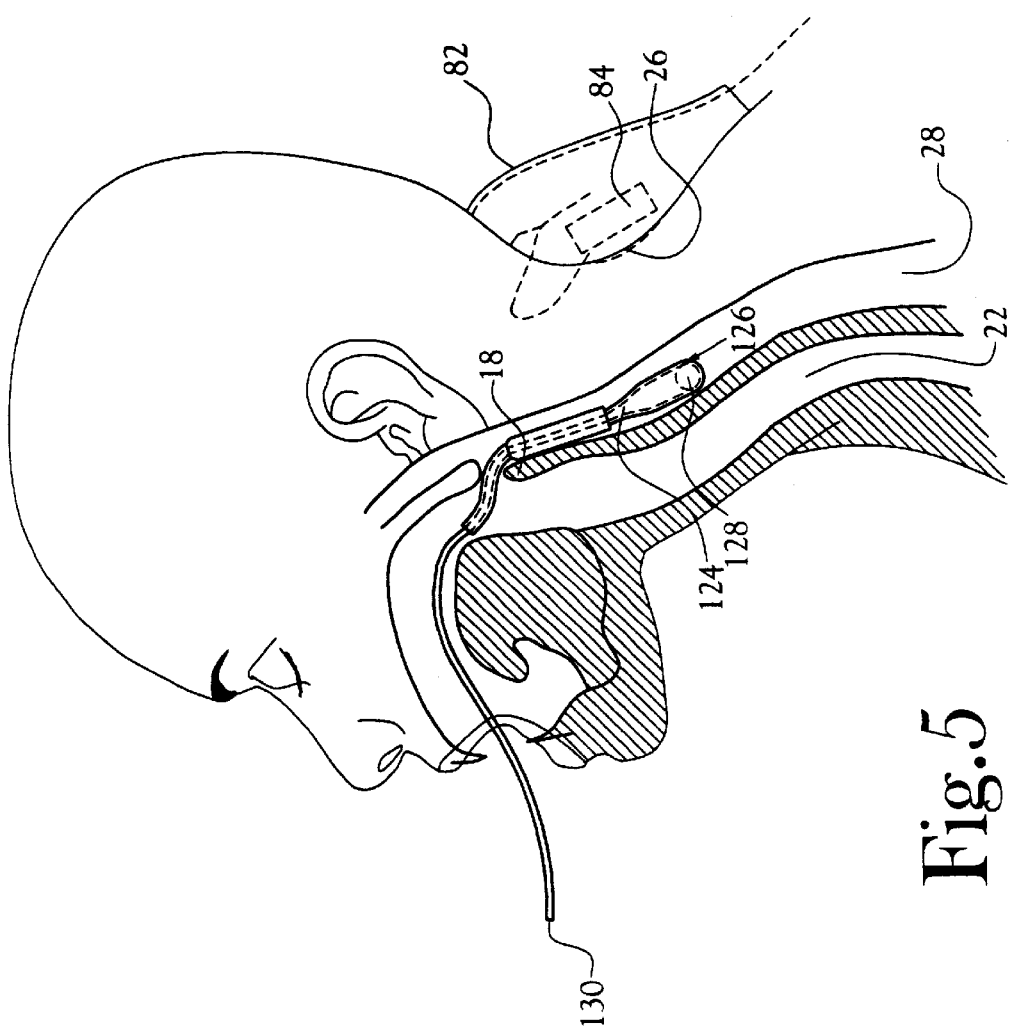

MAGNETICALLY ORIENTING LARYNGEAL ELEVATOR BLADE

CROSS REFERENCE TO RELATED APPLICATIONS

This is a continuation-in-part of application Ser. No. 10/078,133, filed Feb. 19, 2002.

STATEMENT REGARDING FEDERALLY SPONSORED RESEARCH OR DEVELOPMENT

Not Applicable.

BACKGROUND OF THE INVENTION

1. Field of Invention

This invention pertains to intubation devices for insertion into a patient. More particularly, this invention pertains to an intubation apparatus utilizing a magnetic insertion end that is guided to a patient's target passageway by a magnetic field.

2. Description of the Related Art

Prior intubation devices have provided various guide mechanisms to direct a tube into an organ of a patient such as directing a tube through the nose or mouth and into the trachea or esophagus, or inserting a tube through the abdominal wall. Typical prior intubation device include insertion of a guide device such as a guide wire, insertion sheath, and/or guide cylinder, that is inserted into the appropriate body opening. A tube is connected to the guide wire or inserted through the sheath or cylinder for intubation. The intubation process typically includes an operator manipulating a guide wire or tube into the appropriate passageway by rotating, wiggling, turning, and extending, or periodically retracting, the guide device until the tube is inserted into the appropriate passageway. Medical personnel may be trained to utilize a laryngoscope that allows visualization of the glottis and trachea. The intubation process is often attempted by trained attendants and is typically a time-critical process of insertion of an endotracheal tube to provide an unobstructed airway into a patient's trachea. Guiding the endotracheal tube into a trachea includes threading the tube past the epiglottis, through the glottis opening (*rima glottidis*), and past the vocal chords, which is a difficult procedure for trained emergency response personnel who may not practice the procedure often. If the procedure is not completed quickly and properly, the patient may suffer brain injury due to lack of oxygen from a blocked breathing passageway. Any delay in placement of an endotracheal tube may delay performance of additional life-saving procedures on a patient.

There is a need for an intubation apparatus for insertion of a laryngeal elevator including an elongated body without requiring direct visualization of a patient's internal passages during insertion of the elongated body into the appropriate passageway of a patient. A further need includes providing a magnetically orienting laryngeal intubation system that allows insertion of a laryngeal elongated body into an appropriate passageway of a patient with the elongated body bending to facilitate insertion into the preferred channel of a branching internal passageway. An additional need includes a method of insertion of an laryngeal intubation member having a magnetically attracted insertion end that is guided into a preferred internal passageway by magnetically coupling with a magnet field.

BRIEF SUMMARY OF THE INVENTION

According to one embodiment of the present invention, a magnetic oral laryngeal intubation apparatus is disclosed along with a method of insertion of the intubation apparatus into a preferred passageway in a patient, such as the patient's trachea or esophagus. The intubation apparatus includes an elongated body having an insertion end sized to be inserted into an opening in the patient. The elongated body is bendable along its length for insertion into a preferred pathway within the patient. A magnetic member is coupled to the insertion end with the orientation of the magnetic member and insertion end affected by a magnetic field positioned external and proximal to the patient. The external magnetic field is manipulated to affect the orientation of the magnetic member within the patient in order to guide the magnetic member and insertion end into the preferred passageway within the patient. One embodiment includes the magnetic member having a ferro-magnetic member movably attached to the insertion end. An additional embodiment includes the magnetic member having a spherical magnet flexibly coupled to the insertion end for movement of the spherical magnet relative to the insertion end. A further embodiment includes the magnetic member being rotatable within a tube member attached to the insertion end when the magnetic member is influenced by the external magnetic field. When the magnetic member and insertion end are guided by the external magnetic field into the preferred passageway, a tube is guided along the elongated body for intubation into the preferred passageway without direct visual viewing of the progress of the tube into a preferred passageway within the patient.

A method of insertion of a magnetic laryngeal body into a patient includes the steps of using a bendable elongated body including an insertion end having a magnetic member pivotably connecting thereon, positioning the insertion end into an opening in the patient, and adjusting an internal position of the magnetic member and the insertion end by positioning a magnetic field external of the patient. A step of adjusting includes remotely adjusting the internal position of the insertion end laterally and longitudinally within the patient by manipulating the external magnetic field relative to the patient body. The manipulating step positions the insertion end of the elongated member into a preferred passageway within the patient. A step of intubating positions a tube into the preferred passageway without direct visual viewing of the progress of the insertion end into the preferred passageway within the patient.

BRIEF DESCRIPTION OF THE SEVERAL VIEWS OF THE DRAWINGS

The above-mentioned features of the invention will become more clearly understood from the following detailed description of the invention read together with the drawings in which:

FIG. 1 is a side perspective view of a magnetic oral laryngeal intubation apparatus of the present invention, positioned for insertion into a patient's mouth;

FIG. 2A is a top view of the intubation apparatus of FIG. 1, with the magnetic member enclosed by a flexible member coupled to the insertion end by a sleeve member;

FIG. 2B is a side perspective view of FIG. 2A;

FIG. 2C is a cross-section view along lines 2C—2C of FIG. 2A;

FIG. 4 is a perspective side view of a step of positioning the intubation apparatus into a trachea of a patient;

FIG. 5 is a side perspective view of a step of positioning the intubation apparatus into an esophagus of a patient;

DETAILED DESCRIPTION OF THE INVENTION

Figure 3A:
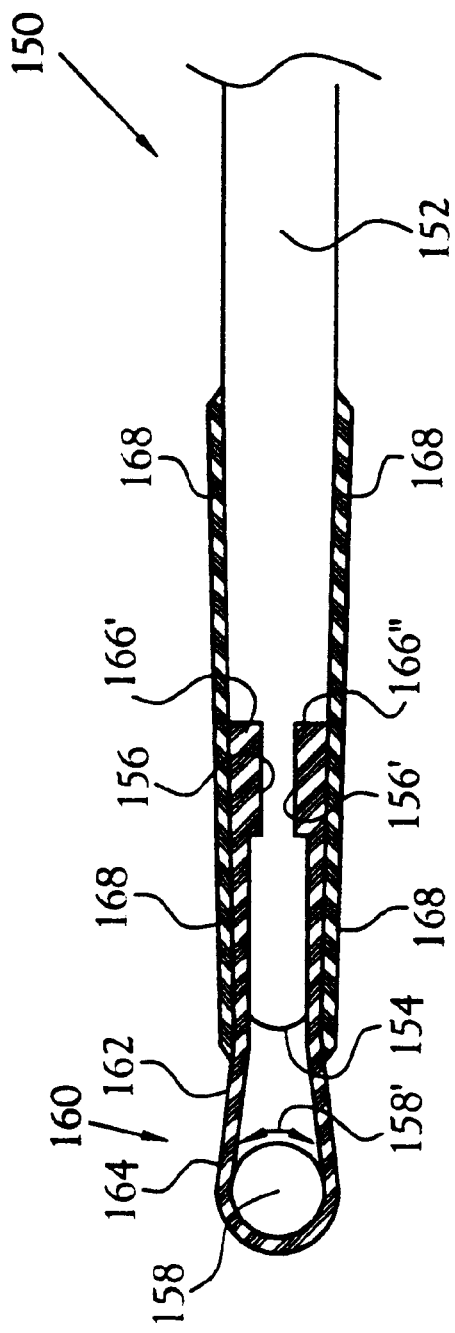
FIG. 3A is a top view of an alternative embodiment of FIG. 1, illustrating an attachment of the sleeve member and the flexible member to an insertion end.

A magnetic oral laryngeal elevator (mole) intubation apparatus 110 is disclosed along with a method for insertion of the intubation apparatus 110 into a preferred pathway within a patient such as a trachea 22 or an esophagus 28. The intubation apparatus 110 includes an elongated body 120 having an insertion end 126 and a magnetic member 128 coupled to the insertion end 126. The orientation of the magnetic member 128 is influenced by a magnetic field positioned proximal to the patient, with the magnetic field manipulated by an operator in order to guide the insertion end 126 into the preferred pathway within the patient. Upon insertion of the insertion end 126 into the preferred pathway, an intubation tube is insertable by guiding the tube along the path of the elongated body 120.

The elongated body 120 is illustrated in FIGS. 1, 2A and 2B and includes an elongated blade body having a lengthwise flexibility and having a magnetic member 128 coupled to the elongated body 120 that is guided during insertion by a magnetic field proximal to the patient, for rapid positioning of the insertion end 126 through a plurality of curved and branched passageways within the patient. An example of an insertion route of the elongated body 120 includes insertion of an insertion end 126 into a patient's mouth 12, past the tongue 14, into the oral cavity 16, past the epiglottis, through the glottis opening 18 (rima glottidis), and past the vocal cords for passage into a preferred passageway such as the trachea 22 or esophagus 28 of a patient. The insertion end 126 is guided by an external magnetic field through the patient's passageways and into the preferred passageway by the magnetic member 128 flexibly coupled across a throat segment gap 124 to a distal end 122 of the elongated body 120. As illustrated in detail in FIGS. 2A and 2B, the magnetic member 128 is enclosed in a flexible member 140 such as a tubular sleeve of material having a rounded, closed enclosure end 144, a flexible throat segment 142, and an open connector end 146 that is joined to the distal end 122. The flexible member 140 is composed of a tubular material such as medical grade silicone or latex rubber or a comparable surgical grade material that is flexible to allow bending laterally and longitudinally. The open connector end 146 is fitted onto the distal end 122, and is extended along the distal end 122 until the flexible connector end 146 fits into a pair of notches 122', 122" that are indented into opposed edges 134', 134" at a selected distance of about one-half inch to about three-quarters of an inch from the distal end 122. The connection into the pair of notches 122', 122" provides a first level of joining of the connection end 146 onto the distal end 122. As illustrated in FIG. 3A, a rim of stiffened material 166', 166" may be formed into an alternative configuration of an open connector end 166 for secure connecting into respective notches 122', 122". FIGS. 2A and 2B illustrate the connector end 146 as encircled and tightly secured around the elongated body 120 by a sleeve 148 that is composed of a heat-shrinkable material such as a polyolefin tubing having an adhesive lined interior. Upon application of heat, or upon application of an alternative means for shrinking, the sleeve 148 is securely joined around the connector end 146 to maintain a second level of joining of the flexible member 140 to the distal end 122 to assure the magnetic member 128 remains connected during insertion, internal maneuvering within the patient, and during removal of the insertion end 126 after completion of the insertion and intubation of a tube into the preferred passageway.

As illustrated in FIGS. 2A and 2C, the elongated body 120 is in the shape of an elongated stylus, also identified herein as an elongated blade, and is flexible along the lengthwise axis due to the blade being composed of a bendable material such as a plastic or nylon polymer having a substantially quadrilateral cross-section with rounded corners (see FIG. 2C). The elongated body 120 includes upper and lower sides 132, 132' that are generally planar and flexible along the lengthwise axis. The longitudinal flexibility of the elongated body 120 is preferably greater that its lateral flexibility. A straightened configuration 136 (see FIG. 2A) is attainable by gripping and pulling on the proximal end 130 and the insertion end 126, although the materials composing the elongated body 120 provide a latent tendency for a bending orientation 138 (see FIGS. 1 and 3C) along the longitudinal axis. The proximal end 130 typically remains outside the patient to allow a properly trained person to guide an intubation tube (not shown) along the length of the elongated body 120 for intubation of the tube along the path of the elongated body 120 and into the passageway in which the insertion end 126 is positioned. The elongated body 120 may be sized in a variety of lengths depending on the distance along the internal passageways through which the insertion end 126 will be inserted. An overall length extending from insertion end 126 to proximal end 130 may be between about a length of twelve inches to a length of about thirty-four inches along the longitudinal axis. The internal structure of the elongated body 120 may alternatively include an internal wire or a material having a curving bias (not shown) oriented along the longitudinal axis of the elongated body 120 to maintain the mid-portion in a slightly curved orientation 138.

Within the end enclosure 144, the magnetic member may include a generally spherical shaped magnet 128 composed of any magnetic material that is self-orienting when in the presence of a magnetic field. One example of a magnetic material is a spherical ball composed of neodymium, iron, and boron. Alternatively, the magnetic member may include a sphere of ferro-magnetic material that is rotatable within the end enclosure 144. The throat segment gap 124 may include an internal gap between the magnet 128 and the distal end 122 (see FIGS. 2A and 2B), or an alternative embodiment may provide a limited internal gap between the magnet 128 and the distal end 122 (see FIG. 3A). In an alternative embodiment, the edges 134, 134' of the elongated body 120 near the distal end 122 may include serrated edges (not shown) having teeth directed toward the mid-portion of the elongated body 120, in order to improve the attachment of the connector end 146 of the end enclosure 144 onto the distal end 122. A selected length of about one and a half inches in length of the deformable sleeve 148 is positioned to encircle the connector end 146. The deformable sleeve 148 may be physically crimped or may be heat sealed around the notched portion 122', 122" to maintain the connector end 146 from swiveling around the elongated body 120.

In order to provide an insertion end 126 that is quickly oriented to maneuver into a preferred passageway at internal branched junctions, the flexible throat segment 142 may preferably include therein a throat segment gap 124 of a spaced-apart gap of about one-quarter inch to about one-half inch in length. The throat segment gap 124 allows the flexible throat segment 142 to bend laterally, pivot longitudinally, and/or twist in relation to the distal end 122, and allows the magnet 128 to pivot with the end enclosure 144. Further, upon providing a sphesical magnet 128 having a lubricating material such as talc within the end enclosure 144, the gap segment allows the magnet 128 to rotate 128' without inteffernce by the distal end 122. The magnet 128 may include a plurality of magnets enclosed within the end enclosure 144, with the magnet or magnets typical of magnets known to those skilled in the art and having a north orienting portion and a south orienting portion. The magnet 128 may have a diameter of about the width of the elongated body 120, which may be in the range of about 0.25 inches to about 0.5 inches. The depth of the elongated body 120 may be in the range of about 0.05 inches to about 0.01 inches. Alternatively, the magnet 128 may be cylindrical, elliptical, or a flattened oval shape (not shown) with a width, depth and length sized to allow the magnet to rotate within the flexible enclosure 144. The magnet 128 pivots with the enclosure 144 relative to the distal end 122 in response to one or more externally positioned magnets 80, 84 that are positioned to attract or to repel the magnet 128 into a preferred passageway within the patient. As illustrated in FIGS. 4 and 5, the externally positioned magnets 80, 84 may be positioned proximal to the throat 24 or neck surface 26 of the patient to allow an operator to guide the magnet 128 and insertion end 126 into the trachea 22 or the esophagus 28 without the need for concurrent insertion of a visualization device such as an optic fiber tube. Indirect visualization of the position of the insertion end 126 may be accomplished by incorporation of radiopaque markings along the elongated body 120 and use of radiography techniques known to those skilled in the medical arts.

Figure 3B:
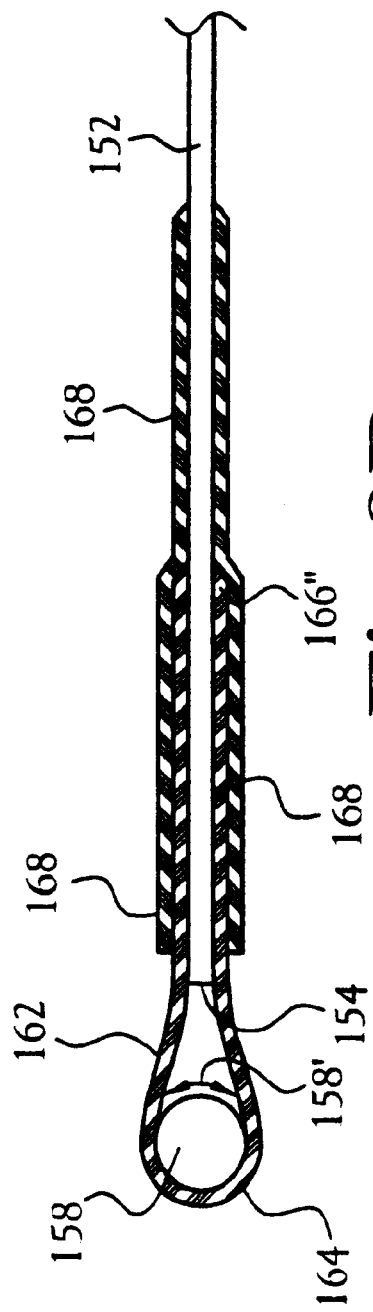
FIG. 3B is a side view of FIG. 3A, illustrating an elongated body having a magnetic member flexibly coupled to the insertion end.

In an alternative embodiment illustrated in FIGS. 3A and 3B, an intubation blade apparatus 150 includes an elongated blade body 152 having a distal end 154 enclosed by a flexible tube member 160. The tube member 160 includes an end enclosure 164 that encircles a magnetic member 158 to allow rotation 158' therein. The tube member 140 includes at least one layer of a medical grade silicon rubber material that extends from the distal end 154. A flexible throat segment 162 includes a spaces-apart internal gap having a limited gap distance between the magnetic member 158 and the distal end 154 of a range of about one-sixteenth inch to about one-fourth inch of separation, and preferably about one-eighth inch of separation. The limited gap length of the throat segment 162 allows a limited range of lateral motion by the magnetic member 158 within the end enclosure 164. Therefore, when the magnetic member 158 moves or pivots within the end enclosure 164, the distal end will be moved nearly in unison with the magnetic member 158. The throat segment 162 may have a width approximately the same as the width of the elongated blade body 152, or may be a lesser or greater width. The throat segment 162 is generally flexible in a range of motion both laterally and longitudinally relative to the distal end 154. Pivoting of the magnetic member 158 due to magnetic coupling with an external magnetic field will successfully direct the distal end 154 into a preferred passageway within the patient, of either the trachea 22 or the esophagus 28, as illustrated in FIGS. 4 and 5. A deformable sleeve 168 forms a binding sheath of material that connects around two dissimilar materials (see FIG. 3A), including the flexible material of the connector end 164 and the nylon polymer material of the elongated blade body 152. The deformable sleeve 168 is configured as a cylindrical sheath of about one and one-half inches in length that encircles a portion of the distal end 154. The connector end 166 includes extension members 166', 166" that extend into a pair of notches 156, 156' indented proximal to the distal end 154. The leg members 166', 166" may be physically crimped around the distal end 154 and the sleeve 168 may be thermally shrink-wrapped around the connector end 166 and leg members 166', 166" to enclose the distal end 154 of the blade body 152.

Figure 7:
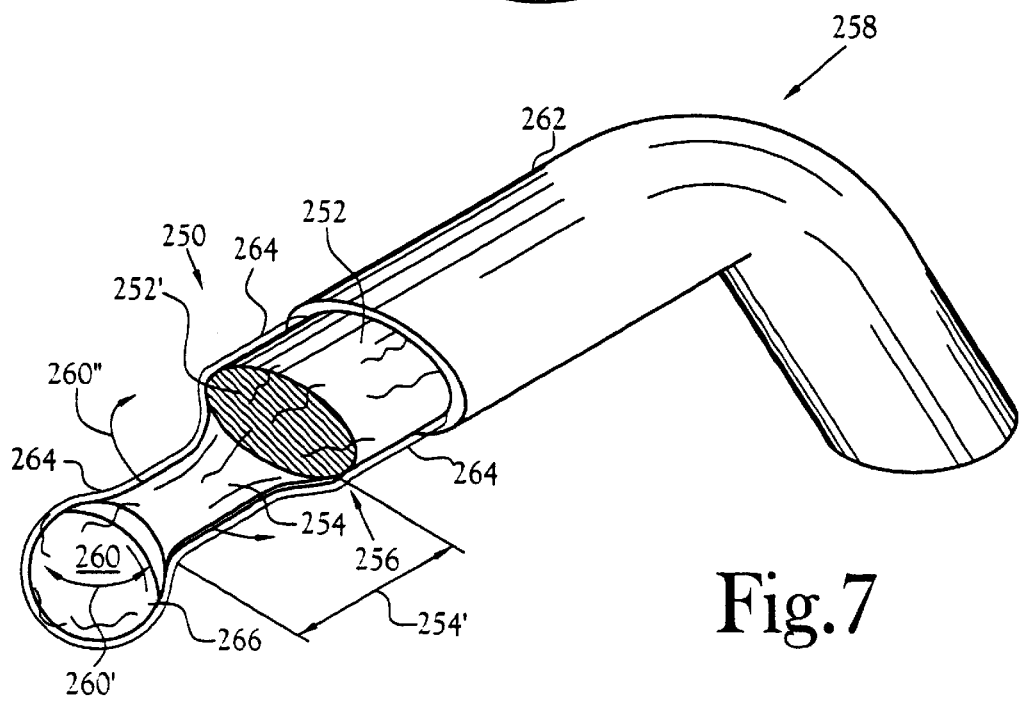
FIG. 7 is a side perspective view of an alternative embodiment of FIG. 1 illustrating a flexible member having an outer cover extended to enclose a rotatable magnet coupled to an insertion end having an elliptical cross-section.

An alternative embodiment is illustrated in FIG. 7, including a laryngeal intubation blade 250 having a cross-section that is cylindrical, oval or elliptical in shape to allow bending along the longitudinal axis of the intubation blade 250 into one of a plurality of bent configurations 258. The elliptical cross-section allows longitudinal flex greater than in a lateral direction for the mid-portion of the blade body 252. An interior 252' of flexible material such as a nylon polymer allows the blade body 252 to bend into one of the plurality of bent configurations 158 when inserted into an opening into the patient, such as the patient's mouth 12 and oral cavity 16 for guidance past the glottic opening 18 and into a preferred pathway such as the trachea 22 or the esophagus 28. The operator may purposefully rotate and manipulate the blade body 252 to insert into a laterally oriented pathway within the patient. A magnet or a ferromagnetic member 260 is rotatably 260' enclosed in a flexible tube-shaped end enclosure 266 connected to the insertion end 256. The end enclosure 266 may be composed of latex rubber or silicon rubber extended from a layer of flexible material 262 that encloses the insertion end 256 and the mid-portion of the blade body 252. The flexible end enclosure 266 allows articulation of the magnet 260 along a flexible throat segment 264, with pivoting 260" of the magnet 260 relative to the insertion end 256. The magnet 260 and throat segment 264 are pivoted during insertion of the insertion end 256 within a patient when the magnet 260 is attracted or repelled by one or more external magnets 80, 84. In an alternative embodiment, a flexible connecting member 254 is enclosed by the throat segment 264, with the connecting member 254 (see FIG. 7) having a narrow throat and a gripping member end that attaches to the magnet 260 to allow pivoting 260" of the magnet laterally and longitudinally in unison with pivoting of the flexible end enclosure 266 relative to the insertion end 256. When attracted or repelled by a magnetic field positioned proximal to the target passageways, the magnet 260 is rotatable 260' and pivotable 260" depending on the movement and orientation of the magnetic field, allowing an operator to externally guide the internal magnet 260 into either the patient's trachea 22 or the esophagus 28, or into another target passageway. The flexible enclosure 266 and throat segment 264 may be composed of silicon rubber material which extends along the offset distance 254' from the blade insertion end 256. The offset distance 254' may be in a range of about 0.125 inches to about 0.5 inches separation from the insertion end 256. An alternative gripping member enclosed by the flexible throat segment 264 can include a spherical or hemispherical shell, or a ring (not shown) of flexible plastic material connecting the magnet 260 to the insertion end 256 enclosed by the flexible material 262.

Figure 6:
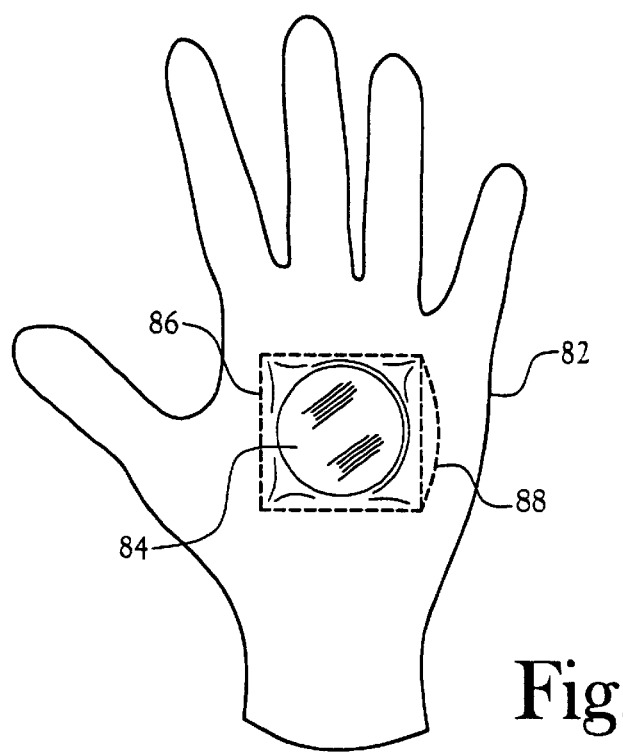
FIG. 6 is a perspective view of a glove having a magnet removably disposed within a pouch in the palm of the glove for positioning against a patient's body.

In order to manipulate and guide the internal movement of the respective magnets 128, 158, 260. and respective insertion ends 126, 154, 256, an external magnet 84 may be attached to a right glove or a left glove worn by an operator of the oral laryngeal intubation blade 110 or the laryngeal intubation blade 150. One external magnet 84 may be disposed within a pouch 86 attached to the palm area of a glove 82 (see FIG. 6). The operator can wear the glove 82 having the external magnet 84 within the pouch 86 and can move his gloved hand along the exterior dermal surfaces 24 or 26 of the patient's throat and neck in order to manipulate and guide the respective magnets 128, 158, 260 and respective insertion ends 126, 154, 256 through the respective openings and passageways of the patient such as through the oral cavity 16, past the glottis opening 18 and between the vocal cords for positioning the blade 110, 150 into either the trachea 22 or the esophagus 28. If a different magnetic field is required, the operator can open a pouch cover 88, remove the external magnet 84 and replace the external magnet 84 with another magnet of a similar configuration but having an alternate magnetic field strength.

A method for insertion of a magnetic oral laryngeal intubation apparatus 110 includes a step of using an elongated body 120 having first and second sides 132, 132' that are bendable along the lengthwise axis into one of a plurality of bent curvatures 138 or 158 (see FIG. 3C or FIG. 7). The following steps of the method for insertion include use of the elongated body 120 but it will be understood that an elliptical blade body 250 may be utilized or a cylindrical blade body (not shown) having a magnetic member attached to an insertion end. A step of positioning includes inserting the insertion end 126 into the patient's mouth 12, past the tongue 14 and through the glottis opening 18. A step of adjusting the internal position of the insertion end 126 positioning a magnetic field proximal to the patient, for remotely adjusting the internal position of the insertion end of the elongated body 120. The step of adjusting further includes placing at least one external magnet 80, and/or a second external magnet 84, proximal to an appropriate dermal surface 24, 26 of the patient in order to influence and guide the magnetic member 128 and insertion end 126 in the patient. A step of manipulating includes moving the one or more external magnets 80, 84 along the appropriate dermal surface 24, 26 of the patient in order to guide the insertion end 126 into a preferred passageway of either the trachea 22, or the esophagus 28 within the patient. A step of inserting includes extending a selected length of the elongated body 120 into the preferred passageway 22 or 28 to guide the insertion end 126 of the elongated body 120 toward a target organ in the patient. The method for insertion further includes a step of intubating including inserting an intubation tube along the path of the elongated body 120, wherein the step of intubating positions the intubation tube into the preferred passageway without the operator directly visually viewing the preferred passageway leading to the target organ within the patient. From the foregoing description, it will be recognized by those skilled in the art that the intubation apparatus 110 provides a method of inserting, positioning and remotely manipulating an elongated body 120 with an externally positioned magnetic field for guiding the intubation apparatus 110 into a preferred passageway within the patient without requiring insertion of instruments for direct visualization of the progress of the intubation apparatus 110 in the patient. Indirect visualization of the position of the intubation apparatus 110 may be accomplished by incorporation of radiopaque markings along the elongated body 120.

While the present invention has been illustrated by description of several embodiments and while the illustrative embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept.

Having thus described the aforementioned invention, we claim:

1. An intubation apparatus for guiding a tube into a preferred passageway within a patient, comprising:
    a flexible elongated blade body having an insertion end sized to be inserted into an opening connected with a preferred passageway within the patient, said blade body including a first and second cross-sectional axis being perpendicular and non-equal whereby said blade body is more resistant to flex in a lateral direction than flex in a longitudinal direction;
    a magnetic member rotatably coupled in a flexibly pivoting relationship to said insertion end; and
    a magnetic field positioned external of the patient, said external magnetic field is manipulated to affect the orientation of said magnetic member within the patient;
    whereby upon insertion of said insertion end into the patient, said external magnetic field is positioned to guide said magnetic member rotatably coupled in said flexibly pivoting relationship with said insertion end into the preferred passageway within the patient.

2. The intubation apparatus of claim 1 wherein said magnetic member includes a ferro-magnetic member rotatably enclosed within a flexible tubular member joined to said insertion end.

3. The intubation apparatus of claim 1 wherein said magnetic member includes a spherical magnet rotatably enclosed by a flexible tube segment flexibly coupled to pivot relative to said insertion end thereby said flexible tube segment providing for rotational movement of said magnet within said tube segment during pivoting of said flexible tube segment relative to said insertion end.

4. The intubation apparatus of claim 1 wherein said blade body having an elliptical cross-section and said insertion end includes a flexible member attached thereto, said magnetic member is pivotably attached to said flexible member.

5. The intubation apparatus of claim 4 wherein said flexible member having a base end attachable to said insertion end, said flexible member having a tubular distal end extended a spaced-apart distance from said insertion end, said magnetic member is rotatably enclosed within said flexible member proximal to said distal end.

6. The intubation apparatus of claim 1 wherein said elongated blade body ha a substantially quadrilateral cross-section and including a mid-portion having a longitudinal flex greater than a lateral flex.

7. The intubation apparatus of claim 1 wherein said external magnetic field includes at least one external magnet positioned proximal to a dermal surface of the patient and proximal to said insertion end within the patient, said at least one external magnet is manipulated along the dermal surface proximal to the preferred passageway within the patient into which said magnetic member and said insertion end are to be inserted.

8. The intubation apparatus of claim 7 wherein said insertion end of said elongated blade body is inserted a selected distance into the preferred passageway within the patient whereby a tube is guided along the elongated blade body into the preferred passageway.

9. An intubation apparatus for guiding a tube into a preferred passageway within the patient, comprising:

an elongated blade member having an insertion end sized to be inserted through the patient's mouth, said elongated blade member having a non-circular cross section whereby said blade member is more resistant to bending in a lateral direction than to bending in a longitudinal direction;

a magnetic member including a spherical magnet rotatably coupled to said insertion end for movement of said spherical magnet relative to said insertion end, said spherical magnet is enclosed within a flexible member attached to said insertion end, whereby said spherical magnet is rotatable within said flexible member and is pivotable to move laterally and longitudinally relative to said insertion end;

a magnetic field positioned external of the patient, said external magnetic field is moved proximal to the patient to guide the orientation of said spherical magnet within said tube member alone an internal passageway within the patient:

whereby said insertion end is inserted past the patient's vocal cords with said spherical magnet guided by said external magnetic field positioned proximal to the patient for guidance of said insertion end into a preferred passageway within the patient.

10. The intubation apparatus of claim 9 wherein said external magnetic field includes at least one external magnet positioned against a dermal surface of the patient proximal to the insertion end within the patient, said at least one external magnet is manipulated along the dermal surface proximal to the preferred passageway within the patient into which said magnetic member and said insertion end are to be inserted.

11. The intubation apparatus of claim 9 wherein said flexible member attached to said insertion end includes a said tube segment coupled at a first end on said insertion end, said tube segment having a distal portion forming said flexible member having said magnetic member attached thereto, said magnetic member is disposed to rotate within said flexible member and to induce pivoting of said throat segment relative to said insertion end when said spherical magnet is in the presence of said external magnetic field positioned proximal to the patient.

12. The intubation apparatus of claim 11 wherein said flexible member including a base end attachable to said insertion end, said flexible member having a distal end extended a spaced-apart distance from said insertion end, said magnetic member is rotatably enclosed within said flexible member proximal to said distal end, said flexible member is pivotable along said spaced-apart distance relative to said insertion end.

13. The intubation apparatus of claim 12 wherein said flexible member base end is attachable to said insertion end by a deformable sleeve disposed to enclose said base end of said flexible member and said insertion end of said elongated blade member, said deformable sleeve extends a sufficient length from said insertion end and along said elongated blade member to securely bond said flexible member base end to said elongated blade member.

14. An intubation apparatus for insertion into an internal passageway within a patient, comprising:

an elongated body having an insertion end sized for intubation into a patient, said elongated body that is bendable about its longitudinal axis; and a magnet rotatably enclosed within a flexible member attached to said insertion end of said elongated body, said rotatable magnet is pivotable relative to said insertion end when in the presence of an external magnetic field positioned proximal to the patient;

whereby said insertion end is inserted into the internal passageway within the patient, said rotatable magnet is pivotable relative to said insertion end when in the presence of said external magnetic field manipulated by the operator in order to position said insertion end into a preferred passageway within the patient.

15. The intubation apparatus of claim 14 wherein flexible member includes a tube member having a base end attached to said insertion end, said tube member is bendable relative to said insertion end, said tube member base end is attached to said insertion end by a deformable sleeve disposed to enclose said base end of said tube member arid said insertion end of said elongated body, said deformable sleeve extends a sufficient length from said insertion end to enclose said base end for securely bonding said base end to said elongated body.

16. The intubation apparatus of claim 15 wherein said external magnetic field includes at least one external magnet positioned against a first dermal surface of the patient proximal to the internal passageway through which said insertion end is inserted, said at least one external magnet is manipulated along the first dermal surface of the patient for guidance of said insertion end into the preferred passageway within the patient.

17. The intubation apparatus of claim 16 wherein said external magnetic field further includes a second external magnet positioned against a second dermal surface of the patient proximal to the internal passageway through which said insertion end is inserted, said second external magnet is manipulated along a second portion of the dermal surface of the patient for guidance of said insertion end into the preferred passageway within the patient.

18. A method for insertion of a tube guided by a magnetic laryngeal intubation body into a preferred passageway within a patient, comprising the steps of:

using a bendable elongated body including an insertion end having a magnetic member rotatably enclosed by a flexible member pivotably connecting to said insertion end;

positioning said insertion end of said bendable elongated body through the patient's oral cavity;

adjusting the direction of said insertion end by positioning a magnetic field external of the patient, said step of adjusting including remotely adjusting an orientation of said rotatable magnetic member within said flexible member and remotely pivoting said flexible member relative to said insertion end to move laterally and longitudinally within the patient;

manipulating said external magnetic field along the patient's dermal surface, said manipulating step guiding said insertion end into a preferred passageway within the patient; and inserting a selected length of said bendable elongated body into the preferred passageway within the patient.

19. The method for insertion of claim 18 further comprising a step of intubating by inserting a tube along the path of said bendable elongated body, wherein said step of intubating positions said tube into the preferred passageway without direct visual viewing of the preferred passageway within the patient.

20. An apparatus for guiding an intubation tube into a preferred pathway within the patient, comprising:

an elongated body having an insertion end sized to be insertable into an opening in the patient, said elongated body having a non-circular cross section bendable along its longitudinal axis for insertion into a preferred pathway within the patient;

a flexible member pivotably connected at a base end to said insertion end, said flexible member is connected to said insertion end by a deformable sleeve disposed to enclose said base end of said flexible member and to enclose a sufficient length of said insertion end to bond said flexible member base end to said insertion end;

a magnetic member rotatably coupled with said flexible member, said magnetic member is pivotable laterally and longitudinally in relation with said flexible member relative to said insertion end; and a magnetic field positioned external to the patient, said external magnetic field is manipulated to affect the orientation of the magnetic member within the patient;

whereby upon insertion of said insertion end into the patient, said external magnetic field is positioned to guide said magnetic member and said flexible member pivotable laterally and longitudinally with resulting guidance of said insertion end into the preferred pathway within the patient.

21. The apparatus of claim 20 wherein said magnetic member includes a rotatable magnet enclosed by said flexible member, said rotatable magnet is pivotable in the presence of said external magnetic field positioned proximal to a dermal surface of the patient, whereby said rotatable magnet and said insertion end are guided into a preferred internal pathway in the patient in response to the operator's manipulation of said external magnetic field positioned proximal to the patient.

22. The apparatus of claim 21 wherein said external magnetic field includes an external magnet disposed within a palm portion of a glove wearable by the operator, said glove having said external magnet thereon is positioned along an exterior dermal surface of the patient to manipulate by magnetic attraction between said external magnet and said rotatable magnet for insertion of said insertion end into the preferred pathway within the patient.

* * * * *